United States Patent [19]
Cushman

[11] Patent Number: 5,920,911
[45] Date of Patent: Jul. 13, 1999

[54] EARCUP SOFT-SEAL WITH THINNED LIPS AND INTERLEAVING LAYERS OF DAMPING MATERIALS

[75] Inventor: William Bradford Cushman, Pensacola, Fla.

[73] Assignee: Poiesis Research, Inc., Pensacola, Fla.

[21] Appl. No.: 08/972,217

[22] Filed: Nov. 17, 1997

[51] Int. Cl.[6] .................................................. A42B 1/06
[52] U.S. Cl. .................................. 2/209; 2/423; 181/129
[58] Field of Search ............................... 2/209, 203, 423, 2/455; 128/864; 181/129; 379/433

[56] References Cited

U.S. PATENT DOCUMENTS

| | | | |
|---|---|---|---|
| 1,333,012 | 5/1920 | Aileo ............................................ | 2/209 |
| 3,506,980 | 4/1970 | Aileo . | |
| 3,593,341 | 7/1971 | Aileo ............................................ | 2/209 |
| 3,875,592 | 4/1975 | Aileo ............................................ | 2/209 |
| 3,944,018 | 3/1976 | Satory .......................................... | 2/209 |
| 4,905,322 | 3/1990 | Aileo et al. ................................. | 2/209 |
| 5,020,163 | 6/1991 | Aileo et al. ................................. | 2/209 |
| 5,138,722 | 8/1992 | Urella et al. ................................ | 2/209 |
| 5,400,296 | 3/1995 | Cushman et al. . | |
| 5,500,958 | 3/1996 | Falco ........................................... | 2/209 |
| 5,747,549 | 5/1998 | Tsurugai et al. ........................... | 521/60 |

OTHER PUBLICATIONS

Physical & Applied Acoustics an Introduction by Erwin Meyer & Ernst–Georg Neumann Section 1.4.

*Primary Examiner*—John J. Calvert
*Assistant Examiner*—Tejash D Patel

[57] ABSTRACT

A high performance hearing protection or communications earcup and seal is disclosed that takes advantage of the facts that a characteristic acoustic impedance mismatch at a boundary will reflect a large portion of impinging energy rather than absorb it, and the "pumping" action on an elastomeric boundary from cyclic acoustic pressure can be damped by placing damping materials adjacent to that boundary. The preferred embodiment of the hearing protection earcup seal of the instant invention interleaves damping materials between the plurality of concentric ring structures of the instant invention and places thinned edges on individual concentric ring structures to enhance seal conformation with obstacles such as eyeglass temple pieces. An elastomeric semi-annular tensile plate supports the concentric ring structures of the instant invention. Both the earcup and earcup seal of the instant invention are readily manufacturable with conventional tooling.

9 Claims, 3 Drawing Sheets

Fig. 10
Fig. 11
Fig. 12
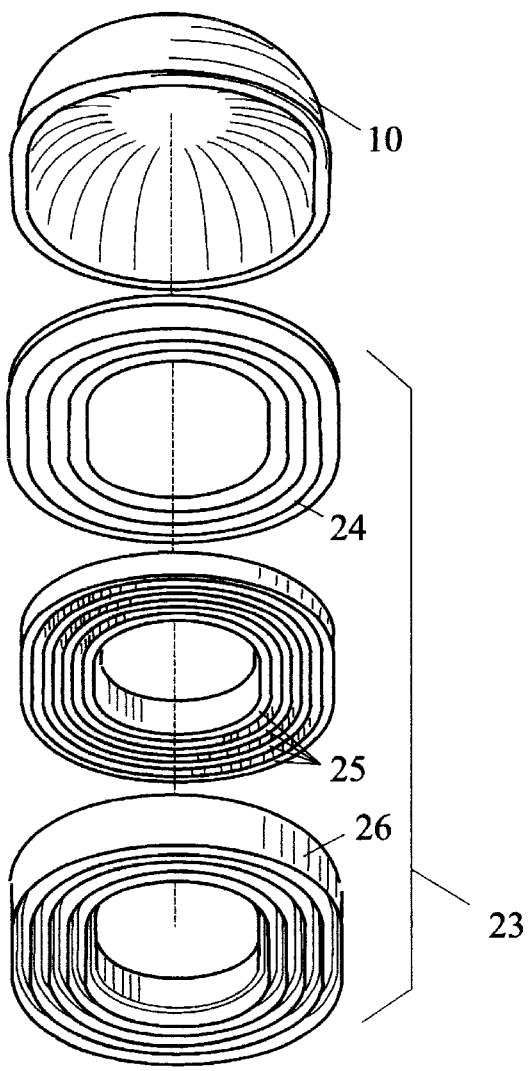
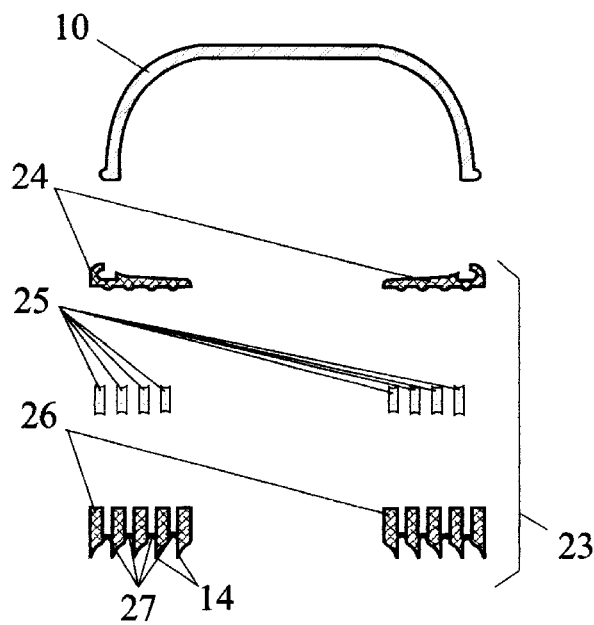
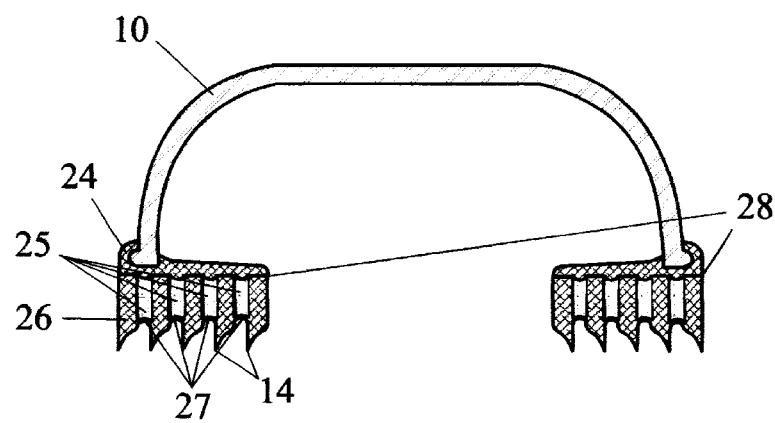

EARCUP SOFT-SEAL WITH THINNED LIPS AND INTERLEAVING LAYERS OF DAMPING MATERIALS

BACKGROUND OF THE INVENTION

1. Field of the Invention

This invention relates to high-performance hearing protection or communications earcups and seals, more particularly to hearing protection or communications earcups and soft seals that may be manufactured with a minimum number of operations while providing excellent acoustic protection as well as a comfortable contact surface for the user.

2. Description of Related Art

Earcups are widely used in both industry and in the military. Recently, Poiesis Research, Inc., of Pensacola, Fla., working with the U. S. Navy Aerospace Medical Research Laboratory at Pensacola, Fla., demonstrated an advanced passive earcup and seal design with over 45 dB of attenuation at 100 Hz. This earcup was made possible by advances in materials science described in U.S. Pat. No. 5,400,296 issued to Cushman, et al. As it is generally acknowledged within the hearing protection field that any more than 50 dB of attenuation would be masked by bone conduction and, therefore, superfluous, this earcup and seal come very close to being "perfect." These test results were, however, obtained in a laboratory situation and may not reflect conditions in the real world. The earcup seal was placed against a polished stainless-steel flat-plate coupler that had been lightly coated with vacuum grease to preclude gas leaks at the contact surface. It is impractical to assume that users of any earcup design will be willing to apply a coat of grease to insure a gas-tight seal against their uneven head. These laboratory data show that under ideal conditions an earcup and seal can perform very well indeed and suggest that the earcup part of the combination requires little improvement in terms of performance. The soft seal between the earcup and the user's head can be improved considerably, however, and improvements in the manufacturability of both the earcup and the soft seal can be realized.

Some form of soft-seal is necessary in any earcup design to allow the earcup and seal to accommodate to the idiosyncrasies of individual head contours. Currently marketed earcup seals fall generally into two categories: those using an envelope filled with an open-celled foam and those using an envelope containing a liquid or gel. Earcup seal envelopes are usually made from vinyl or urethane film. In all cases the seal envelope has a characteristic acoustic impedance that differs from air and will reflect a great percentage of the impinging energy because of this impedance difference.

The characteristic acoustic impedance for a particular material is calculated by multiplying the density of the material times the speed of sound within the material, which results in impedance, Z, in Rayls. Characteristic acoustic impedance mismatches always cause some portion of the impinging acoustic pressure to be reflected, thus attenuating that portion transmitted past the mismatched boundary. The ratio of acoustic reflections at any interface between two media can be calculated if the characteristic acoustic impedances of the two materials is known using the following formula, taken from Erwin Meyer and Ernst-Georg Neumann in their text *Physical and Applied Acoustics, an Introduction*, Academic Press, 1972, Section 1.4, transmission line theory. The impedances of water and air are used to illustrate.

$$\text{Reflection Factor} = \frac{Z_{Air} - Z_{Water}}{Z_{Air} + Z_{Water}} = -0.99944$$

Water at a boundary with air is a very good acoustic reflector.

An earcup seal made from a vinyl envelope containing a liquid would have impedance mismatches at the outer surface between air and vinyl; the inner surface of the envelope between vinyl and the liquid; the inner surface of the envelope between the liquid and vinyl; and, finally, the outer surface of the envelope between vinyl and air. Of course, the magnitude of the impedance mismatch between vinyl and a liquid is much less than between vinyl and air. A similar impedance mismatch analysis can be made for a foam-filled earcup seal within a vinyl envelope.

Open-celled foams are known acoustic attenuators at high frequencies. This is because acoustic pressure forces air to pass through small pores in open cell foam where the air flow becomes turbulent and gives rise to viscous damping. As the wavelength becomes long relative to the thickness of foam used, however, the slope of the pressure differential becomes shallow and viscous damping is diminished. For viscous damping to be maximally effective there should be at least ½ wavelength present within the foam.

Sound travels at roughly 344 meters per second in air. A foam sample thickness of 2.5 centimeters will lose effectiveness for wavelengths longer than about 5 centimeters. That is, a foam sample thickness of 2.5 centimeters will lose effectiveness for frequencies below about 6880 Hertz. To be effective down to the lower-end frequency threshold for human hearing, at about 20 Hertz, an open-cell foam type of earcup seal would have to be 8.6 meters thick. These data suggest that an earcup seal containing an open-celled foam would perform extremely poorly, and earcup seals of this design do not. However, experience shows that if the envelope surrounding the open-celled foam is removed performance is extremely poor. If the reverse experiment is made, and the envelope alone is used, performance is also extremely poor. These results arise because it is the interaction of the foam with the seal envelope that is producing damping. Even though the wavelength of impinging acoustic energy may be very long relative to the envelope-to-foam interface, the envelope film is thin and has little inertia so it will be "pumped" diaphragmatically by impinging energy, thus resulting in cyclical "rubbing" of the envelope film against the foam interface to produce slip damping.

Liquid or gel-filled earcup seals perform in a similar fashion. As the envelope film is "pumped" by cyclical acoustic pressures viscous damping at the interface between the envelope membrane and the liquid or gel takes place. Liquids and gels themselves are excellent conductors of acoustic energy.

In light of the above discussion it should be clear that adding more liquid or more foam or both will not substantially improve the performance of an earcup seal, but adding more impedance mismatched layers perpendicular to acoustic pathways most certainly will. Aileo exploited an impedance mismatching principle in his U.S. Pat. No. 3,506,980 in which a series of concentric rings and interleaving air form an earcup seal with multiple impedance mismatches at each ring surface. Adding more impedance mismatched layers in slip damping contact with foam or fiber inserts or gel or liquid filled chambers is an even better approach that has been taken with the instant invention.

In the design of an earcup and seal consideration must also be given to how an earcup seal with make contact with both the earcup and the person using it. Air leaks between the seal and earcup or between the seal and the head of the person using it are good pathways for acoustic energy. Both pathways degrade performance significantly. Finally, any design must be manufacturable to be practical, and a minimum number of injection moldable parts is distinctly desirable, as is ease of assembly.

BRIEF SUMMARY OF THE INVENTION

Accordingly, an object of the instant invention is to provide an improved earcup and seal that provides high performance protection.

Another object of the instant invention is to provide an easily manufactured earcup and seal.

Another object of the instant invention is to provide an improved earcup seal that is comprised of a plurality of impedance mismatched layers arranged perpendicular to the normal acoustic pathway.

Another object of the instant invention is to provide an improved earcup seal that is easily attached to and sealable with an associated earcup.

Another object of the instant invention is to provide an improved earcup seal that is comfortable for a user to wear.

Another object of the instant invention is to provide an improved earcup seal that seals well with a user's head.

A further object of the instant invention is to provide an improved earcup seal that exploits viscous or slip damping interactions induced by cyclic "pumping" of a plurality of barrier layers.

These and additional objects of the invention are accomplished by an earcup and seal with the seal formed into a plurality of concentric rings of material, separated by air spaces or by spaces filled with fiber, foam, liquid, or gel material; suspended on and joined to a semi-annular elastomeric tension plate; with each concentric ring being formed into a thinned-shape, or slitted sections, or webbed sections at the contact surface that would normally be placed against a user's head to facilitate sealing against the user's head; and with the tension plate of the earcup seal being joined to the earcup of the instant invention with adhesive or elastomeric structures; and with the earcup of the instant invention being manufacturable in one injection-molding operation, and with the tension plate and concentric rings of the seal of the instant invention being manufacturable in one injection-molding operation for one embodiment of the instant invention; and with the tension plate, concentric rings and damping fibers, foam, liquid, or gel being manufacturable in a minimal number of operations in a second embodiment of the instant invention.

BRIEF DESCRIPTION OF THE DRAWINGS

In the following Description of the Preferred Embodiments and the accompanying drawings, like numerals in different figures represent the same structures or elements. The representation in each of the figures is diagrammatic and no attempt is made to indicate actual scales or precise ratios. Proportional relationships are shown as approximations.

FIG. 10 shows a view of a preferred embodiment of the instant invention expanded to show the separate parts.

FIG. 11 shows a cross-sectional view of a preferred embodiment of the instant invention expanded to show the separate parts.

FIG. 12 shows a cross-sectional view of a preferred embodiment of the instant invention as it would be assembled.

DETAILED DESCRIPTION

The parts indicated on the drawings by numerals are identified below to aid in the reader's understanding of the present invention.

10. Earcup.
11. Concentric ring earcup seal.
12. Concentric ring structures
13. Semi-annular tension plate.
14. Thinned lips.
15. Curved surface.
16. Communications earcup.
17. Earphone transducer.
18. Semi-annular tension plate reinforcement.
19. Surface.
20. Section of an eyeglass temple piece.
21. Slits.
22. Thinned web sections.
23. Seal with damping fibers, foam, liquid, or gel.
24. Semi-annular tension plate.
25. Damping fibers, foam, liquid, or gel.
26. Concentric ring structures with attaching membranes.
27. Concentric ring attachment membranes.
28. Glue line.

Figure 1:
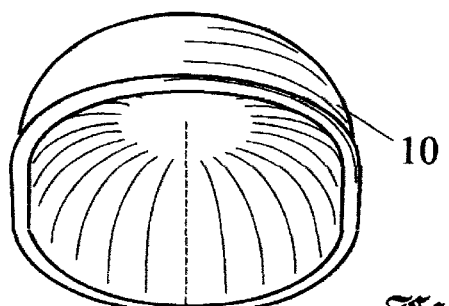
FIG. 1 shows a view of an embodiment of the instant invention expanded to show two separately manufacturable parts.

FIG. 1 shows a view of an embodiment of the instant invention expanded to show two separately manufacturable parts. In FIG. 1, 10 is an earcup of the instant invention and 11 is an earcup seal of the instant invention.

Figure 2:
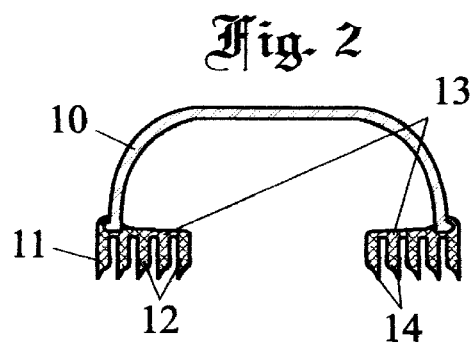
FIG. 2 shows a cross-sectional view of an embodiment of the instant invention shown in FIG. 1 when assembled.

FIG. 2 shows a cross-sectional view of an embodiment of the instant invention shown in FIG. 1 when assembled. In FIG. 2, 10 is an earcup of the instant invention; 11 is an earcup seal of the instant invention; 12 are concentric ring structures of the instant invention; 13 is a semi-annular tension plate of the instant invention; and 14 are thinned lips on the edges of the concentric ring structures of the instant invention.

Figure 3:
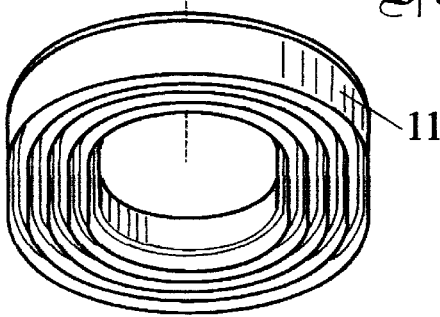
FIG. 3 shows a cross-sectional view of an embodiment of the instant invention shown in FIGS. 1 and 2 as it may appear when placed against a curved surface.

FIG. 3 shows a cross-sectional view of an embodiment of the instant invention shown in FIGS. 1 and 2 as it may appear when placed against a curved surface. In FIG. 3, 10 is an earcup of the instant invention; 11 is an earcup seal of the instant invention; 12 are concentric ring structures of the instant invention; 13 is a semi-annular tension plate of the instant invention; 14 are thinned lips on the edges of the concentric ring structures of the instant invention; and 15 is a curved surface. The curvature of curved surface, 15, causes the thinned lips, 14, to compress or fold and the central concentric ring structures, 12, to rise upward relative to FIG. 3. When the central concentric ring structures of FIG. 3 rise upward the central portion of the semi-annular tension plate, 13, is placed in "hoop" tension and resists the upward rise. Adjustment of the elastomeric qualities of the semi-annular tension plate, 13, will, therefore, control the resistance of the semi-annular tension plate to deformation and, subsequently, the relative pressure of the central concentric ring structures and thinned sections against the curved surface. There are three distinct advantages to the use of an elastomeric semi-annular tension plate as described in the instant invention rather than a hard backing plate affixed to the earcup. First, the use of an elastomeric semi-annular tension plate as part of the design contributes significantly to the comfort of the earcup and seal for the wearer as the pressure of the concentric rings against the wearer's curved head can be essentially equalized across concentric rings with appropriate choice of elastomeric materials and dimensions. Second, the use of an elastomeric semi-annular tension plate makes it possible to incorporate the tension plate as part of the concentric rings and thinned sections using the same elastomeric material, thus allowing the entire earcup seal structure to be molded as a single piece in this embodiment of the instant invention. Third, eliminating the need for a hard backing plate as part of the earcup eliminates the need for multiple parts of the earcup which typically must be glued together.

Figure 4:
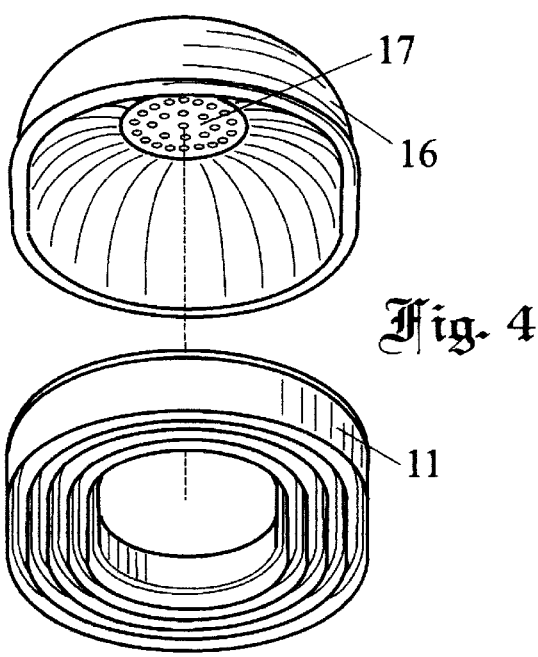
FIG. 4 shows a view of an embodiment of the instant invention as a communications earcup expanded to show separately manufacturable parts.

FIG. 4 shows a view of an embodiment of the instant invention as a communications earcup expanded to show separately manufacturable parts. In FIG. 4, 16 is a communications earcup of the instant invention; 11 is an earcup seal of the instant invention and 17 is an earphone transducer of the instant invention.

Figure 5:
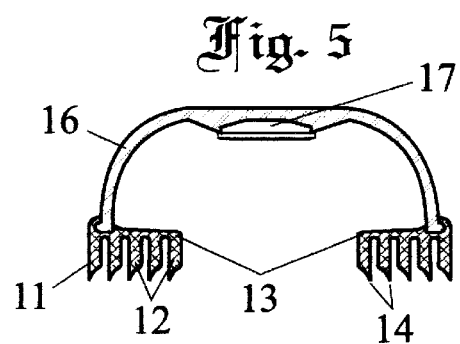
FIG. 5 shows a cross-sectional view of an embodiment of the instant invention shown in FIG. 4 when assembled.

FIG. 5 shows a cross-sectional view of an embodiment of the instant invention shown in FIG. 4 when assembled. In FIG. 5, 16 is a communications earcup of the instant invention; 11 is an earcup seal of the instant invention; 12 are concentric ring structures of the instant invention; 13 is a semi-annular tension plate of the instant invention; 14 are thinned lips on the edges of the concentric ring structures of the instant invention; and 17 is an earphone transducer of the instant invention. In FIGS. 4 and 5 the earphone transducer is shown firmly fixed to the communications earcup of the instant invention by adhesive or other means. By mechanically coupling the mass of the earphone transducer with the mass of the communications earcup the total mass of the combination is made available to resist movement of the communications earcup under the influence of acoustic pressure. Pressure induced whole-earcup movement is a significant acoustic pathway. The earcup may block transmitted acoustic energy perfectly, but it relies upon coupling with the earcup seal and its own inertia to prevent it from reconstructing externally impinging acoustic energy on the inside of the earcup as a diaphragm. Added mass exploits Newton's well known relationship: acceleration is directly proportional to force and inversely proportional to mass.

Figure 6:
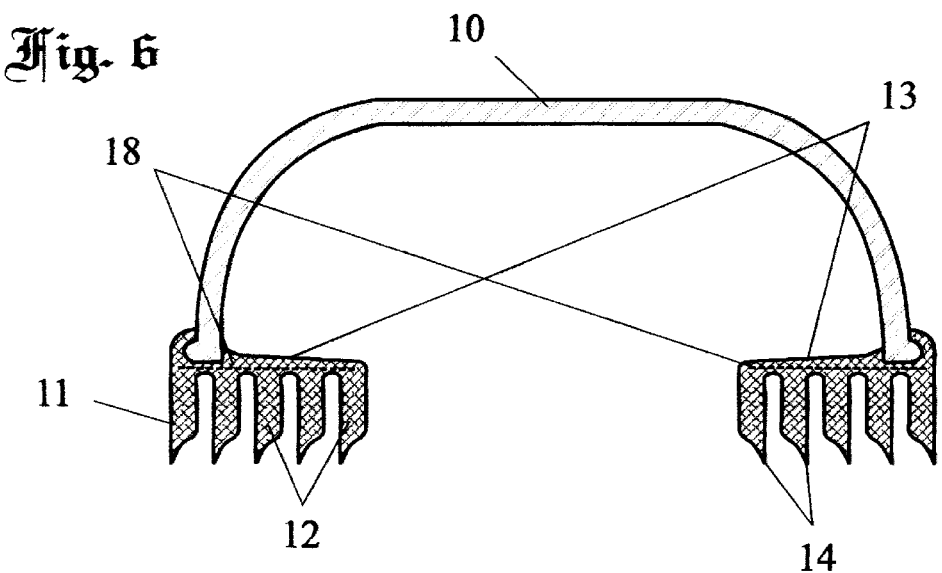
FIG. 6 shows a cross-sectional view of an embodiment of the instant invention with reinforcement in the semi-annular tension plate of the instant invention.

FIG. 6 shows a cross-sectional view of an embodiment of the instant invention with reinforcement in the semi-annular tension plate of the instant invention. In FIG. 6, 10 is an earcup of the instant invention; 11 is an earcup seal of the instant invention; 12 are concentric ring structures of the instant invention; 13 is a semi-annular tension plate of the instant invention; 14 are thinned lips on the edges of the concentric ring structures of the instant invention; and 18 is a semi-annular tension plate reinforcement. The amount of pressure required to deflect the semi-annular tension plate, 13, of the instant invention upward relative to FIG. 6 as it is pressed against a curved or irregular surface is directly proportional to the "hoop" tensile strength of the semi-annular tension plate. The "hoop" tensile strength of semi-annular tension plate, 13 can be enhanced by embedding reinforcing fibers or other structures within the matrix material of the semi-annular tension plate as shown in FIG. 6.

Figure 7:
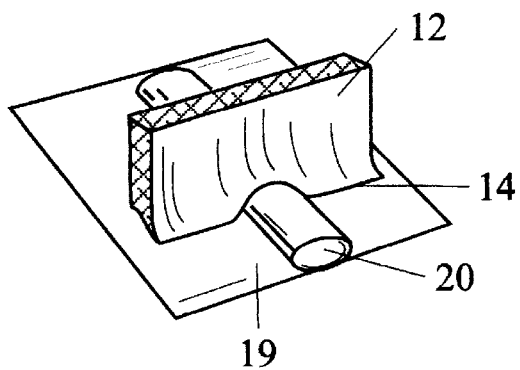
FIG. 7 shows a view of a section of the seal of an embodiment of the instant invention shown in FIGS. 1 through 6 as it may appear when placed against an obstruction such as an eyeglass temple piece.

FIG. 7 shows a view of a section of the seal of an embodiment of the instant invention shown in FIGS. 1 through 6 as it may appear when placed against an obstruction such as an eyeglass temple piece. In FIG. 7, 12 is a section of a concentric ring structure; 14 is a section of a thinned lip; 19 is a surface; and 20 is a section of an eyeglass temple piece. The thinned lip, 14 of FIG. 7 can substantially conform to the shape of the eyeglass temple piece because its reduced thickness makes it more elastomeric locally. Enhanced conformation to obstacles such as an eyeglass temple piece aids in reducing air gaps between the seal and the user's head that are acoustic pathways. Flanking acoustic pathways between the earcup seal and the user's head are a major source of performance loss in any earcup and seal design.

Figure 8:
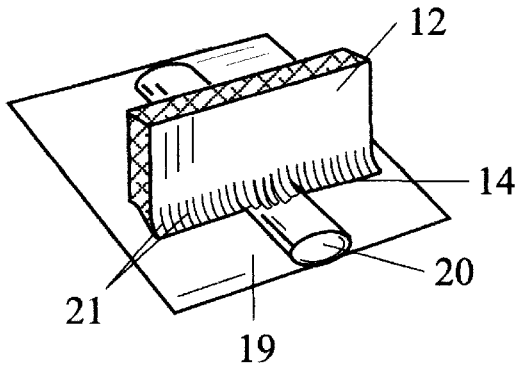
FIG. 8 shows a view of a section of an alternate seal of an embodiment of the instant invention shown in FIGS. 1 through 6 as it may appear when placed against an obstruction such as an eyeglass temple piece.

FIG. 8 shows a view of a section of an alternate seal of an embodiment of the instant invention shown in FIGS. 1 through 6 as it may appear when placed against an obstruction such as an eyeglass temple piece. In FIG. 8, 12 is a section of a concentric ring structure; 14 is a section of a thinned lip; 19 is a surface; and 20 is a section of an eyeglass temple piece. The thinned lip, 14 of FIG. 8 has been cut vertically relative to FIG. 8 to produce a plurality of small slits, 21. A plurality of small slits cut in the thinned lip of concentric ring structures can enhance the ability of the lip to substantially conform to the shape of an obstacle such as an eyeglass temple piece by favoring horizontal deformation relative to vertical deformation (relative to FIG. 8). That is, vertical deformations are not substantially transmitted horizontally to neighboring areas to cause lifting of the thinned lip and increased gap size.

Figure 9:
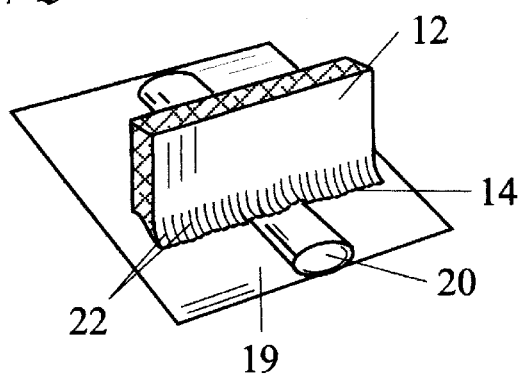
FIG. 9 shows a view of a section of a second alternate seal of a preferred embodiment of the instant invention shown in FIGS. 1 through 6 as it may appear when placed against an obstruction such as an eyeglass temple piece.

FIG. 9 shows a view of a section of a second alternate seal of a preferred embodiment of the instant invention shown in FIGS. 1 through 6 as it may appear when placed against an obstruction such as an eyeglass temple piece. In FIG. 9, 12 is a section of a concentric ring structure; 14 is a section of a thinned lip; 19 is a surface; and 20 is a section of an eyeglass temple piece. The thinned lip, 14 of FIG. 9 has been thinned vertically relative to FIG. 9 to produce a plurality of small thinned web sections, 22. A plurality of small thinned web sections in the thinned lip of concentric ring structures can enhance the ability of the lip to substantially conform to the shape of an obstacle such as an eyeglass temple piece by favoring horizontal deformation relative to vertical deformation (relative to FIG. 9). That is, vertical deformations are not substantially transmitted horizontally to neighboring areas to cause lifting of the thinned lip and increased gap size. Thinning rather than slitting the concentric ring lip enhances blocking of acoustic pathways by closing the slits at the cost of a slight increase in horizontal deformation induced gapping (relative to FIG. 9).

FIG. 10 shows a view of a preferred embodiment of the instant invention expanded to show the separate parts. In FIG. 10, 23 is a seal with interleaving damping fibers, foam, liquid, or gel; 24 is a semi-annular tension plate; 25 is damping fiber, foam, liquid, or gel; and 26 are concentric ring structures with attaching membranes.

FIG. 11 shows a cross-sectional view of a preferred embodiment of the instant invention expanded to show the separate parts. In FIG. 11, 23 is a seal with interleaving damping fibers, foam, liquid, or gel; 24 is a semi-annular tension plate; 25 is damping fiber, foam, liquid, or gel; 26 are concentric ring structures with attaching membranes; 27 are concentric ring attachment membranes; and 14 are thinned lips.

FIG. 12 shows a cross-sectional view of a preferred embodiment of the instant invention as it would be assembled. In FIG. 12, 24 is a semi-annular tension plate; 25 is damping fiber, foam, liquid, or gel; 26 are concentric ring structures with attaching membranes; 27 are concentric ring attachment membranes; 14 are thinned lips; and 28 is the glue line where semi-annular tension plate, 24 is adhesively attached to the concentric ring structures with attaching membranes, 26.

The preferred embodiment of the instant invention shown in FIGS. 10 through 12 enhances the performance of the embodiments of the instant invention shown in FIGS. 1 through 6 by interleaving damping fiber, foam, liquid, or gel between the concentric ring structures of the instant invention. In conventional earcup seal designs a large portion of the impinging acoustic energy is blocked by the interface between the seal and the surrounding air where a characteristic acoustic impedance mismatch occurs, and the remainder is blocked by viscous or slip damping at the interface between the seal membrane and the foam or liquid or gel it contains as the foam or liquid or gel is cyclically "pumped" by acoustic pressure. Increasing the thickness of any of these materials has little, if any, effect. In the instant invention, however, a plurality of interfacing layers is presented to impinging acoustic energy in a manner that is easily manufactured, comfortable to wear, and extremely conformable to obstacles that may be present such as the temple pieces from eyeglasses. Increasing the number of layers increases the points where impedance mismatching and viscous or slip damping can occur. In the preferred embodiment of the instant invention the earcup is made from polypropylene resin or polypropylene resin modified according to the teaching of U.S. Pat. No. 5,400,296 referenced above. The seal should have at least five concentric rings, and the preferred damping material is polypropylene wool or polypropylene open-celled foam. If variations in atmospheric pressure are anticipated in use, the concentric ring attachment membranes, 27, may be pierced to allow pressure equalization.

Many modifications and variations of the present invention are possible in light of the above teachings. For example, a different number of concentric ring structures could be used or different materials could be employed as damping materials. It is therefore to be understood that, within the scope of the appended claims, the instant invention may be practiced otherwise than as specifically described.

I claim:

1. An earcup soft-seal comprised of:
   a: a surface structure for contact with a user's head, with said surface structure mounted to and supported by,
   b: an elastomeric semi-annular tension plate supported on the outer perimeter of said elastomeric semi-annular tension plate by the edge of an earcup, other means, whereby;

forces acting perpendicular to the plane of orientation of said semi-annular tension plate at or near the interior edge of said elastomeric semi-annular tension plate will cause said elastomeric semi-annular tension plate to deform from a generally planer shape to a generally conical shape as the area at or near the interior edge is elastomerically deformed in tension.

2. The earcup soft-seal of claim 1 with thinned lips on the surface of said surface structure intended for contact with a user's head.

3. The earcup soft-seal of claim 1 with thinned lips containing a plurality of small slits on the surface of said surface structure intended for contact with a user's head.

4. The earcup soft-seal of claim 1 with thinned lips containing a plurality of thinned web sections on the surface of said surface structure intended for contact with a user's head.

5. An earcup soft-seal comprised of:
   a: a plurality of at least three layered structures, with said plurality of layered structures being generally disposed semi-annularly around said earcup soft-seal in the area generally between an earcup and an intended user's head, with the surfaces of said layered structures oriented generally perpendicular to acoustic pathways between said earcup and said intended user's head, and with
   b: interleaving layers of damping materials disposed between the layers of said plurality of layered structures, whereby, when layered structures are deflected by acoustic pressure said deflection is transferred to said interleaving damping materials.

6. The earcup soft-seal of claim 5 with a plurality of thinned lips on the surface of said earcup soft-seal intended for contact with a user's head.

7. The earcup soft-seal of claim 5 with a plurality of thinned lips containing a plurality of small slits on the surface of said earcup soft-seal intended for contact with a user's head.

8. The earcup soft-seal of claim 5 with a plurality of thinned lips containing a plurality of thinned web sections on the surface of said earcup soft-seal intended for contact with a user's head.

9. The earcup soft-seal of claim 5 with said damping materials made from polypropylene resin.

* * * * *